US008993226B2

(12) United States Patent
Madson

(10) Patent No.: US 8,993,226 B2
(45) Date of Patent: Mar. 31, 2015

(54) METHOD OF TESTING FOR A MILK TRISACCHARIDE

(75) Inventor: Michael Madson, Garner, IA (US)

(73) Assignee: BioLogistics. LLC, Garner, IA (US)

( * ) Notice: Subject to any disclaimer, the term of this patent is extended or adjusted under 35 U.S.C. 154(b) by 64 days.

(21) Appl. No.: 13/426,891

(22) Filed: Mar. 22, 2012

(65) Prior Publication Data

US 2013/0031965 A1 Feb. 7, 2013

Related U.S. Application Data

(60) Provisional application No. 61/513,921, filed on Aug. 1, 2011.

(51) Int. Cl.
| | |
|---|---|
| C12Q 1/00 | (2006.01) |
| G01N 33/00 | (2006.01) |
| G01N 33/20 | (2006.01) |
| G01N 37/00 | (2006.01) |
| G01N 33/04 | (2006.01) |
| G01N 30/88 | (2006.01) |

(52) U.S. Cl.
CPC ........ *G01N 33/04* (2013.01); *G01N 2030/8836* (2013.01)
USPC ............................. 435/4; 73/61.52; 73/61.43

(58) Field of Classification Search
CPC ........... A23V 2002/00; A23V 2250/28; A61K 31/702; A61K 39/0011; A61K 31/00; C08L 5/00; A23C 19/0328; A23C 19/054; A23C 9/1216; A23C 9/20
See application file for complete search history.

(56) References Cited

U.S. PATENT DOCUMENTS

| | | |
|---|---|---|
| 2007/0105179 A1 | 5/2007 | Madson |
| 2009/0104603 A1* | 4/2009 | Satomaa et al. ................. 435/6 |

OTHER PUBLICATIONS

Tao et al., Journal of Dairy Science, vol. 91, 2008, pp. 3768-3778.*
Tao et al, Journal of Dairy Science, vol. 92, 2009, pp. 2991-3001.*
Cataldi et al., Analytica Chimica Acta, vol. 485, Issue 1, May 26, 2003, pp. 43-49.*
Stepans et al. Breastfeeding Medicine, vol. 1, No. 4, 2006.*
Ward, Open Glycoscience, 2009, 2, 9-15.*
Messer, Biochem. J. (1974) 139, 415-420.*
Jaakko Parkkinen and Jukka Finne; Occurrence of N-Acetylglucosamine 6-Phosphate in Complex Carbohydrates; The Journal of Biological Chemistry; Sep. 15, 1985; pp. 10971-10975; vol. 260, No. 20 issue; The American Society of Biological Chemists, Inc.; USA.
Rudiger W. Veh, Jean-Claude Michalski, Anthony P. Corfield, Michael Sander-Wewer, Dagmar Gies, and Roland Schauer; New Chromatographic System for the Rapid Analysis and Preparation of Colostrum Sialyloligosaccharides; Journal of Chromatography; 1981; pp. 313-322; Elsevier Scientific Publishing Company, The Netherlands.
Tadao Saito and Takatoshi Itoh; Variations and Distributions of O-Glycosidically Linked Sugar Chains in Bovine k-Casein; Abstract; pp. 1768-1774; vol. 75; Journal of Dairy Science, Japan, 1992.
Pramod K. Gopal and H.S. Gill; Oligosaccharides and Glycoconjugates in Bovine Milk and Colostrum; British Journal of Nutrition; 2000; pp. S69-S74; vol. 84, Suppl 1: New Zealand Dairy Research Institute; New Zealand.
Harsharnjit S. Gill and M.L. Cross; Anticancer Properties of Bovine Milk; British Journal of Nutrition; 2000; pp. S161-S166; vol. 84, Suppl 1; Institute of Food, Nutrition and Human Health; New Zealand.
Fangyu Hu, Kazuo Furihata, Mie Ito-Ishida, Shuichi Kaminogawa, and Masaru Tanokura; Nondestructive Observation of Bovine Milk by NMR Spectroscopy: Analysis of Existing States of Compounds and Detection of New Compounds; Journal of Agricultural and Food Chemistry; 2004; pp. 4969-4974; vol. 52, No. 16; The University of Tokyo; Japan.
William A. Bubb, Tadasu Urashima, Kuniaki Kohso, Tadashi Nakamura, Ikichi Arai and Tadao Saito; Occurrence of an Unusual Lactose Sulfate in Dog Milk; carbohydrate research; 1999 pp. 123-128; vol. 318; Elsevier Science Ltd.; The Netherlands.

* cited by examiner

*Primary Examiner* — Chris R Tate
*Assistant Examiner* — Douglas F White
(74) *Attorney, Agent, or Firm* — Zarley Law Firm, P.L.C.

(57) ABSTRACT

A method of testing for a trisaccharide in milk includes the step of providing a predetermined amount of milk. The method also includes the step of isolating a trisachharide of the milk with a hydride insertion reaction to identify the molecule as phosphorylated. Also included in the method is the step of obtaining a mass spectrum of the isolated milk trisaccharide sample. The method further includes the step of identifying a molecular structure of the isolated milk trisaccharide sample.

17 Claims, 3 Drawing Sheets

METHOD OF TESTING FOR A MILK TRISACCHARIDE

CROSS REFERENCE TO RELATED APPLICATIONS

This application claims the benefit of U.S. Provisional Application No. 61/513,921, filed Aug. 1, 2011.

BACKGROUND OF THE INVENTION

This invention relates to a method of testing for a milk trisaccharide. More specifically, the present invention relates to a laboratory method that can be used in order to isolate a bovine milk trisaccharide.

Cancer is a disease that affects millions of families and individuals every year. As a result scientists are in a continuous search for substances that are effective in promoting anti-cancer activity whether the substances prevent the onset of cancer or alternatively slow down or stop the growth of cancer.

Thus, a principal object of the present invention is to provide a method for isolating a bovine milk trisaccharide in order to determine the trisaccharide's anti-cancer activity.

SUMMARY OF THE INVENTION

A method of testing for a trisaccharide in milk. The method includes the step of providing a predetermined amount of milk. The method also includes the step of isolating a trisacchharide of the milk, to obtain a sample, and by hydride insertion to help identify the milk trisaccharide. Also included in the method is the step of obtaining a mass spectrum of the isolated milk trisaccharide sample. The method further includes the step of identifying a molecular structure of the isolated milk trisaccharide sample.

DESCRIPTION OF THE PREFERRED EMBODIMENT

Figure 1:
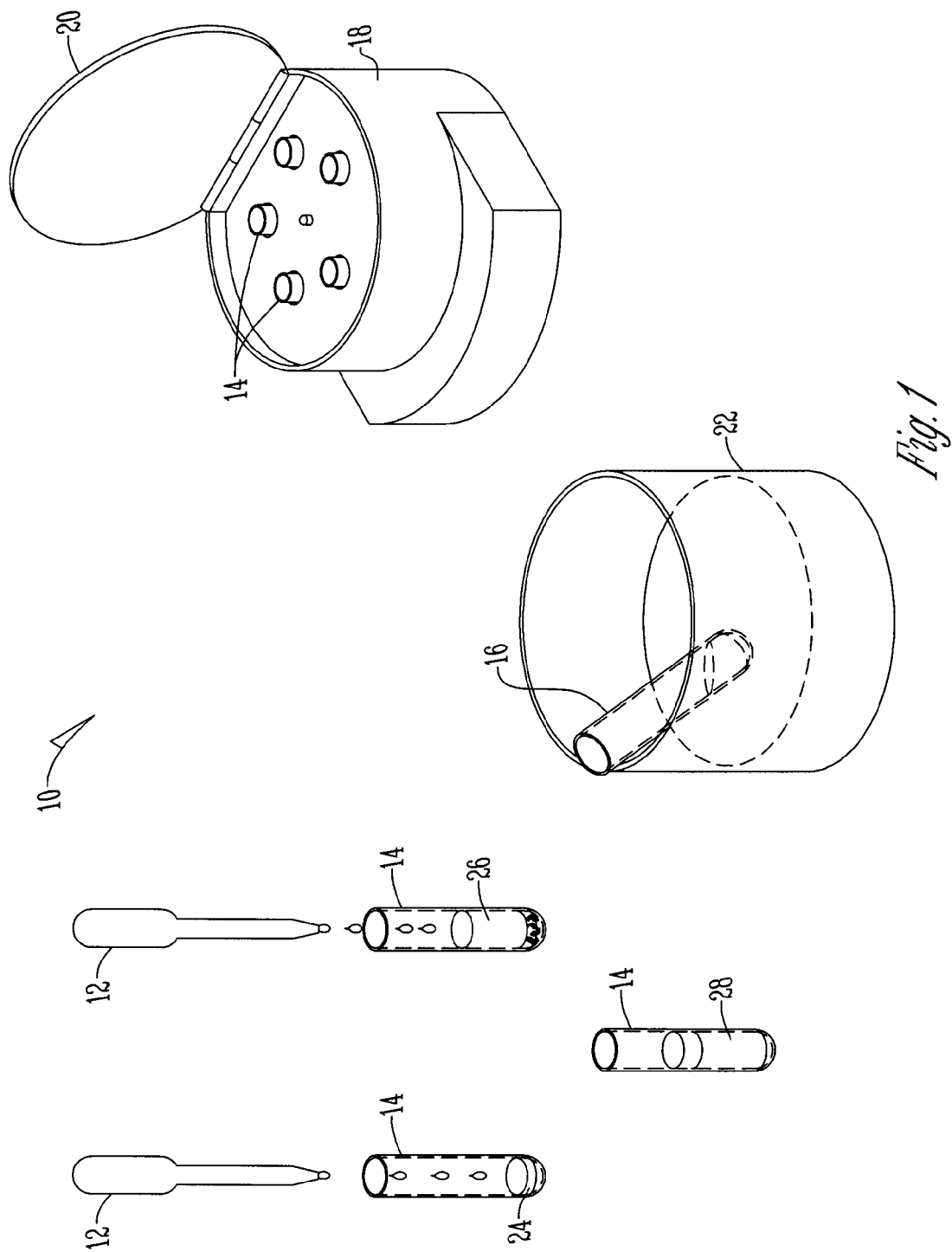
FIG. 1 is a perspective view of the system of isolating a milk trisaccharide of the present invention.
Figure 2:
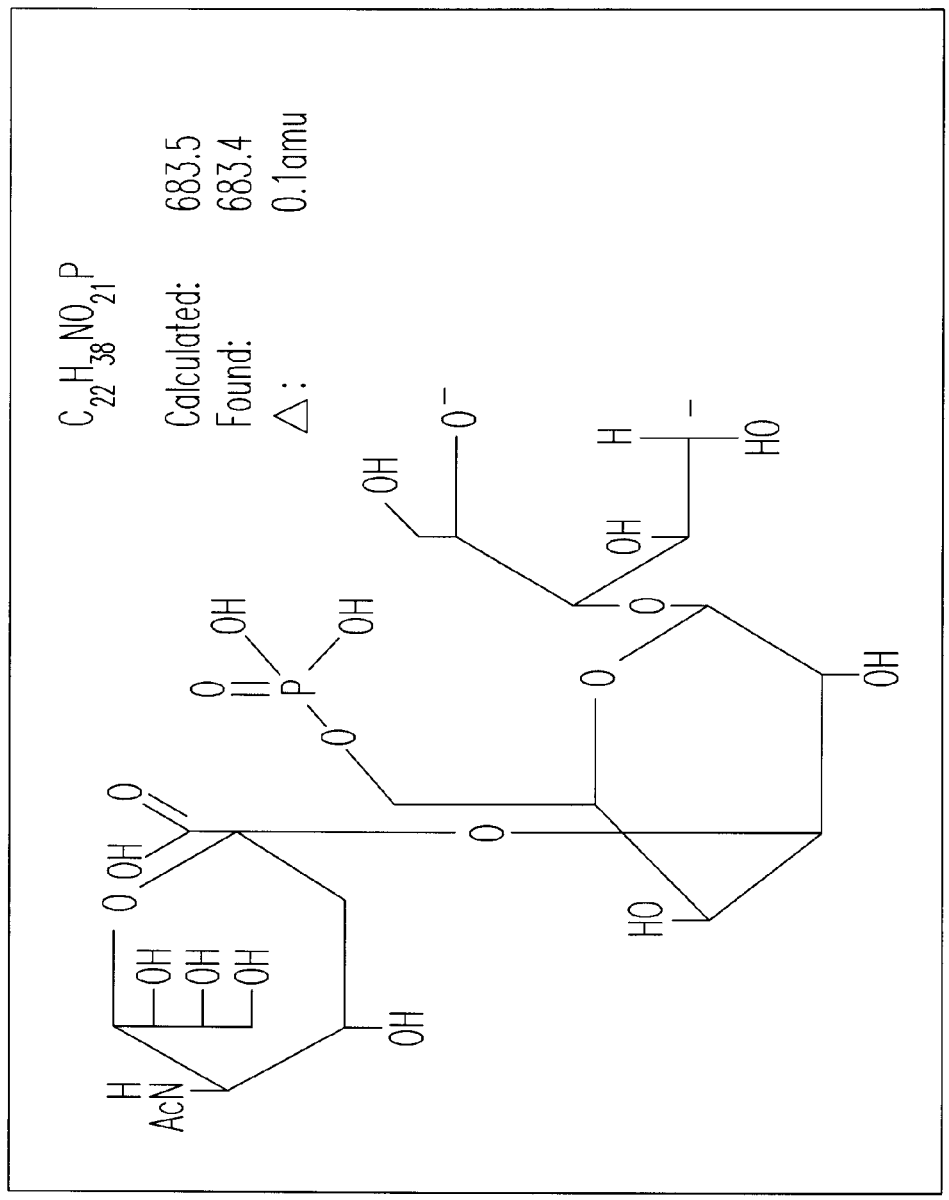
FIG. 2 is a diagram of the fragmentation of the complete molecular ion of a sample of milk trisaccharide identified and isolated by the system of testing for a milk trisaccharide of the present invention.

The figures show a system 10 utilized in order to isolate a bovine milk trisaccharide. The system 10 includes a pipet 12, first and second centrifuge tubes, 14, 16, that in a preferred embodiment are plastic, and a centrifuge 18 having a cap 20 disposed thereon. In addition the system can include a freezer or a container holding water 22.

The method used to isolate the bovine milk trisaccharide using the system 10 is to pipet a predetermined amount of commercialized pasteurized cold fat free milk 24 into the centrifuge tube 14. In a preferred embodiment 0.1 ml commercial pasteurized cold fat free milk 24 is pipet into a 15 ml plastic centrifuge tube 14. Once the commercialized pasteurized cold fat free milk 24 is in the centrifuge tube 14, 1 ml of cold 95% ethanol 26 is added. Thus, a 10:1 ratio of 95% ethanol 26 to the commercialized pasteurized cold fat free milk 24 is presented. At this time the centrifuge tube 18 is capped and centrifuged for a predetermined amount of time, preferably 30-40 seconds.

After centrifuging the supernatant 28 is formed and is placed in a second centrifuge tube 16. The supernatant 28 is then dried with a stream of nitrogen and placed in a freezer 22 for storage. The sample 28 can later be dissolved in water.

Figure 3:
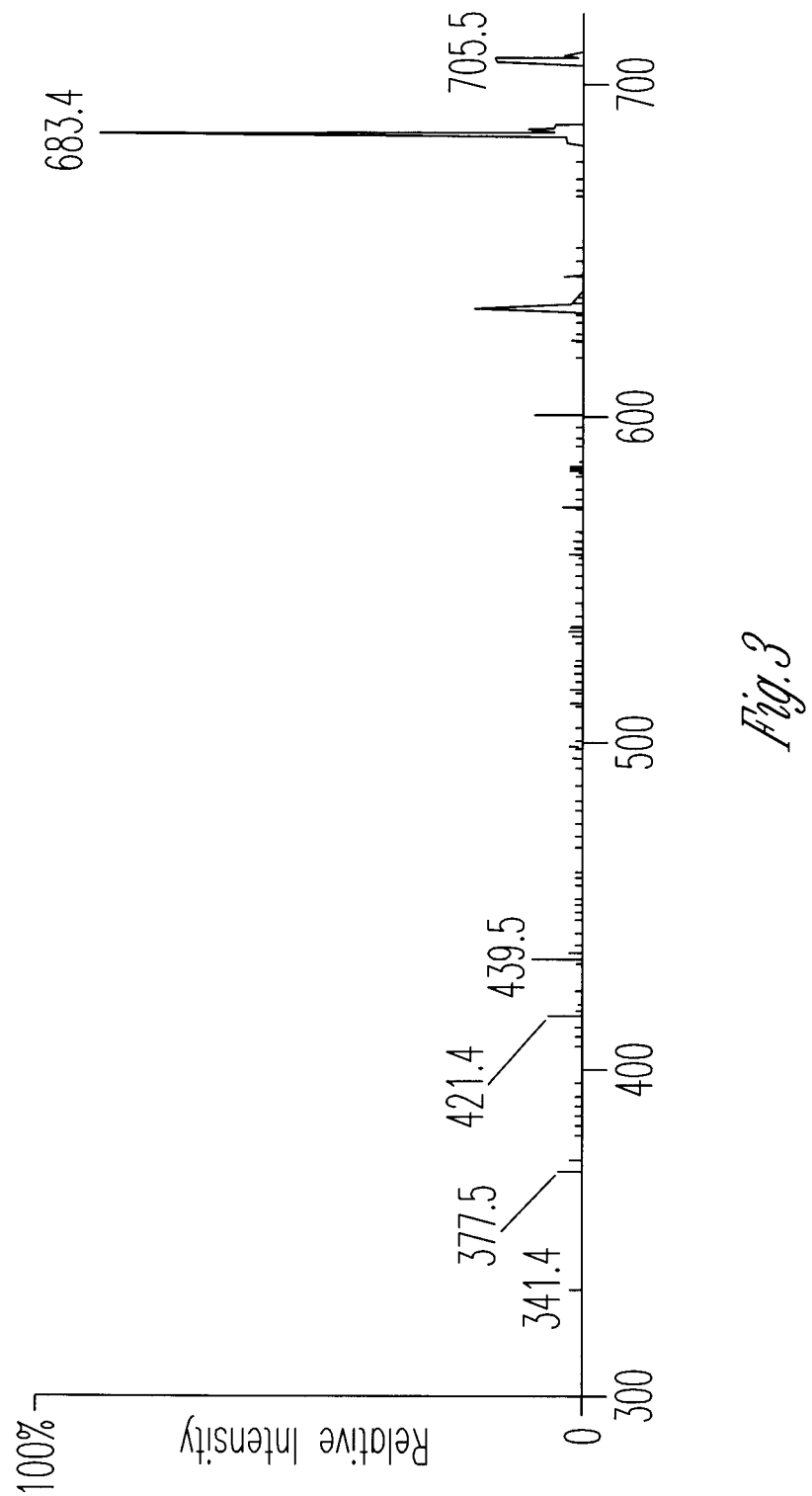
FIG. 3 is a diagram of a mass spectrum of a sample of the isolated milk trisaccharide identified by the system of testing for a milk trisaccharide of the present invention.

A mass spectrum of this sample 28 presents a major ion, m/z 683.3 that is a cross ring cleavage product of the actual ion that is found in the original spectrum of milk fraction. M/Z 705.5 meanwhile is sodium salt as identified in FIG. 3. Thus, this sample is a trisaccharide of bovine milk 30 that contains N-Acetyl neuraminic acid substituted lactosyl-6' phosphate. From mass spectrometry, HPLC and a hydride reduction the trisaccharide was identified and the identity of the substitution position of phosphate is presented. Specifically, the molecule is phosphorylated that is discerned by utilizing a hydride reduction insertion. Thus, by isolating this milk trisaccharide, this milk fraction can be tested for anti cancer activity. Thus, at least all of the stated problems have been overcome.

What is claimed is:

1. A method of testing for a trisaccharide in milk comprising the steps of:
    providing a predetermined amount of milk;
    combining the predetermined amount of milk with ethanol, wherein the ethanol and milk are combined in a 10:1 ethanol to milk ratio;
    isolating a trisaccharide from the milk and ethanol combination to obtain a sample;
    obtaining a mass spectrum of the isolated milk trisaccharide sample; and
    identifying a molecular structure of the isolated milk trisaccharide sample, wherein the identified structure is 3'-N-acetyl neuraminyll lactose 6'-phosphate.

2. The method of testing for a trisaccharide in milk of claim 1 additionally comprising the step of subjecting the isolated milk trisaccharide sample to high performance chromatography.

3. The method of testing for a trisaccharide in milk of claim 1 wherein the trisaccharide is isolated by a hydride reduction comprised of the step of centrifuging the milk and ethanol combination to form a supernatant.

4. The method of testing for a trisaccharide in milk of claim 3 wherein the hydride reduction is used to determine phosphorylation of the isolated milk trisaccharide sample.

5. The method of testing for a trisaccharide in milk of claim 1 wherein the milk is pasteurized fat free bovine milk.

6. The method of testing for a trisaccharide in milk of claim 1 wherein the ethanol is cold 95% ethanol.

7. The method of testing for a trisaccharide in milk of claim 4 wherein the supernatant is comprised of the isolated milk trisaccharide sample.

8. The method of testing for a trisaccharide in milk of claim 3 further comprising the step of identifying a structure of a molecular ion of the isolated milk trisaccharide sample.

9. The method of testing for a trisaccharide in milk of claim 1 wherein the step of identifying the molecular structure of the isolated milk trisaccharide sample comprises identifying a substitution position of a phosphate from the structure of the molecular ion of the isolated milk trisaccharide sample.

10. The method of testing for a trisaccharide in milk of claim 1 further comprising the step of determining whether the trisaccharide molecule is phosphorylated based upon the molecular structure of the isolated milk trisaccharide sample.

11. The method of testing for a trisaccharide in milk of claim 1 further comprising freezing the isolated milk trisaccharide after drying.

12. The method of testing for a trisaccharide in milk of claim 11 further comprising the step of dissolving the frozen isolated milk trisaccharide in water.

13. The method of testing for a trisaccharide in milk of claim 1 wherein the predetermined amount of milk and ethanol are centrifuged for 30-40 seconds.

14. The method of testing for a trisaccharide in milk of claim 1 further comprising drying the sample after isolation.

15. A method of testing for a trisaccharide in milk comprising the steps of:
providing a predetermined amount of milk;
combining the predetermined amount of milk with ethanol, wherein the ethanol and milk are combined in a 10:1 ethanol to milk ratio;
centrifuging the combined predetermined amount of milk and ethanol to form a supernatant;
drying the supernatant;
obtaining a mass spectrum of the supernatant sample; and
identifying a molecular structure of the supernatant sample;
wherein the identified structure is 3'-N-acetyl neuraminyll lactose 6'-phosphate.

16. The method of testing for a trisaccharide in milk of claim 1 further comprising the step of subjecting the isolated milk trisaccharide sample to high performance liquid chromatography before obtaining the mass spectrum of the supernatant sample.

17. A method of testing for a trisaccharide in milk comprising the steps of:
providing a predetermined amount of bovine milk;
combining the predetermined amount of bovine milk with ethanol, wherein the ethanol and milk are combined in a 10:1 ethanol to milk ratio;
centrifuging the combined predetermined amount of bovine milk and ethanol to isolate an isolated bovine milk trisaccharide;
drying the isolated bovine milk trisaccharide;
obtaining a mass spectrum of the isolated bovine milk trisaccharide;
identifying a molecular structure of the isolated bovine milk trisaccharide;
determining whether the trisaccharide molecule is phosphorylated based upon the molecular structure of the isolated milk trisaccharide.

* * * * *